(12) United States Patent
Farooqui et al.

(10) Patent No.: US 10,485,457 B2
(45) Date of Patent: Nov. 26, 2019

(54) DEVICE CONNECTABLE TO A DIALYSIS CATHETER FOR IN SITU ANALYSIS

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Mahfooz Alam Farooqui, Riyadh (SA); Ghassan Al Ghamdi, Riyadh (SA)

(73) Assignees: National Guard Health Affairs, Riyadh (SA); King Saud bin Abdulaziz University for Health Services, Riyadh (SA); King Abdullah International Medical Research Center, Riyadh (SA)

( * ) Notice: Subject to any disclaimer, the term of this patent is extended or adjusted under 35 U.S.C. 154(b) by 215 days.

(21) Appl. No.: 15/455,609

(22) Filed: Mar. 10, 2017

(65) Prior Publication Data

US 2018/0256085 A1    Sep. 13, 2018

(51) Int. Cl.
*A61B 5/145* (2006.01)
*A61M 1/28* (2006.01)
(Continued)

(52) U.S. Cl.
CPC ...... *A61B 5/14503* (2013.01); *A61B 5/14532* (2013.01); *A61B 5/14539* (2013.01);
(Continued)

(58) Field of Classification Search
CPC ............ A61B 5/14503; A61B 5/14532; A61B 5/14539; A61B 5/14546; A61B 5/4839;
(Continued)

(56) References Cited

U.S. PATENT DOCUMENTS 5,836,924 A * 11/1998 Kelliher ............... A61J 15/0015
604/248
7,833,157 B2    11/2010 Gottlieb et al.
(Continued)

FOREIGN PATENT DOCUMENTS

| | | |
|---|---|---|
| CN | 203763560 U | 8/2014 |
| IN | 201201478 I1 | 12/2015 |
| KR | 2015 070922 A | 6/2015 |

OTHER PUBLICATIONS

National Institute of Diabetes and Digestive and Kidney Diseases, "Treatment Methods for Kidney Failure: Peritoneal Dialysis", https://www.niddk.nih.gov/health-information/health-topics/kidney-disease/treatment-methods-for-kidney-failure-peritoneal-dialysis/Pages/facts.aspx, 12 Pages total, (Jan. 2016).
(Continued)

*Primary Examiner* — Daniel L Cerioni
(74) *Attorney, Agent, or Firm* — Oblon, McClelland, Maier & Neustadt, L.L.P.

(57) ABSTRACT

The present invention relates to a device configured with an analyte sensor to measure analytes through an existing peritoneal dialysis catheter and to a method for using the device and to a method for changing of a dialysis protocol in a patient undergoing peritoneal dialysis using the device.

17 Claims, 3 Drawing Sheets

(51) Int. Cl.
*A61M 39/10* (2006.01)
*A61M 39/24* (2006.01)
*A61B 5/00* (2006.01)
*A61M 1/16* (2006.01)

(52) U.S. Cl.
CPC ........ *A61B 5/14546* (2013.01); *A61B 5/4839* (2013.01); *A61B 5/6852* (2013.01); *A61M 1/1605* (2014.02); *A61M 1/285* (2013.01); *A61M 39/10* (2013.01); *A61M 39/24* (2013.01); *A61M 2230/005* (2013.01); *A61M 2230/208* (2013.01); *A61M 2230/50* (2013.01)

(58) Field of Classification Search
CPC ... A61B 5/6852; A61M 1/1605; A61M 1/285; A61M 39/10; A61M 39/24
USPC ........................................................ 600/309
See application file for complete search history.

(56) References Cited

U.S. PATENT DOCUMENTS

| | | | | |
|---|---|---|---|---|
| 2003/0057108 | A1* | 3/2003 | Sridharan | A61B 5/14535 205/775 |
| 2004/0034324 | A1* | 2/2004 | Seese | A61M 1/285 604/246 |
| 2004/0147871 | A1* | 7/2004 | Burnett | A61B 5/14276 604/9 |
| 2004/0193094 | A1* | 9/2004 | Kraus | A61M 27/006 604/8 |
| 2006/0030833 | A1* | 2/2006 | Harris | A61B 5/0422 604/503 |
| 2006/0058731 | A1* | 3/2006 | Burnett | A61M 1/1678 604/29 |
| 2014/0083872 | A1* | 3/2014 | Fuerst | A61B 5/14532 205/792 |
| 2014/0378793 | A1 | 12/2014 | Kamath et al. | |
| 2015/0011855 | A1* | 1/2015 | Burnett | A61M 1/28 600/365 |
| 2016/0051135 | A1* | 2/2016 | Greenberg | A61B 1/307 600/115 |
| 2017/0326284 | A1* | 11/2017 | Dulsner | G06F 19/3481 |
| 2017/0347926 | A1* | 12/2017 | Farooqui | A61B 5/14503 |

OTHER PUBLICATIONS

Patolsky, F., et al., "Nanowire Sensors for Medicine and the Life Sciences", Nanomedicine, vol. 1, No. 1, pp. 51-65, (2006).

Oliver, N.S., et al., "Glucose Sensors: A Review of Current and Emerging Technology", Diabetic Medicine, vol. 26, pp. 197-210 (2009).

Dexcom Continuous Glucose Monitoring, "Dexcom G5 Mobile CGM System", URL: https://www.dexcom.com/g5-mobile-cgm, 8 Pages total, (2017).

Medtronic Diabetes, "Enlite Sensor", URL: http://www.medtronicdiabetes.com/products/enlite-sensor, 2 Pages total, (2017).

World Precision Instruments, "Glucose Sensors", URL: https://www.wpiinc.com/product-listers/glucose-sensors/, 2 Pages total, (2017).

* cited by examiner

DEVICE CONNECTABLE TO A DIALYSIS CATHETER FOR IN SITU ANALYSIS

BACKGROUND OF THE INVENTION

Technical Field

The present invention relates to a device configured with an analyte sensor to measure analytes through an existing peritoneal dialysis catheter.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Renal dysfunction or failure and, in particular, end-stage renal disease, causes the body to lose the ability to remove water and minerals and excrete harmful metabolites, maintain acid-base balance, and control electrolyte and mineral concentrations within physiological ranges. Toxic uremic waste metabolites including urea, creatinine, uric acid, and phosphorus accumulate in the body's tissues, which can result in a person's death if the filtration function of the kidney is not replaced.

Dialysis is commonly used to replace kidney function by removing these waste toxins and excess water. In one type of dialysis treatment, hemodialysis, toxins are removed from a patient's blood externally in a hemodialysis machine. Blood passes from the patient through a dialyzer separated by a semi-permeable membrane from an externally-supplied dialysate. Waste and toxins dialyze out of the blood through the semi-permeable membrane into the dialysate, which is then discarded. Hemodialysis treatment typically lasts several hours and must be performed under medical supervision three or four times a week, requirements that significantly decrease a patient's autonomy and quality of life. Also, since hemodialysis is performed periodically instead of continuously, the patient's condition and general well-being tend to be poor both immediately before hemodialysis (when toxin levels are high) and after hemodialysis (when electrolytes are imbalanced), resulting in the patient having symptoms that range from nausea and vomiting to edema.

Peritoneal dialysis is a common mode of treatment for patients with kidney failure. The technique requires insertion of a plastic tube (peritoneal dialysis catheter) to be placed surgically in the abdominal cavity of the patients. This cavity is flushed with a solution with high glucose concentration several times a day. High glucose concentration in the fluid draws water and solutes into the peritoneal cavity by osmosis. Some glucose is also absorbed in the process. The amount of fluid and solutes drawn into the peritoneal cavity is dependent on the rapidity with which the glucose is absorbed. This process is studied by a specialized test, called Peritoneal Equilibration Test (PET). This test requires special preparation. Multiple samples of the peritoneal dialysis fluid are taken at different time points. The test necessitates that the patient spend several hours in the peritoneal dialysis unit.

In vivo real time measurement of levels of analytes, such as glucose, creatinine, sodium, potassium, etc. in peritoneal dialysis fluid can enhance physicians' capabilities to understand the peritoneal membrane characteristics. Development of a device which could be inserted through the existing peritoneal dialysis catheter while maintaining sterility of the circuit and means to continue dialysis while the device is in place, will open a new way to study mechanisms which may potentially modify membrane characteristics.

The idea of real time peritoneal dialysis fluid measurement is likely to open up research into the study of peritoneal membrane function. As yet, the peritoneal membrane is considered as a "fixed" membrane based on PET testing, real-time monitoring of the membrane function and the potential to "modify" the function by pharmacological means has never been studied. This technology will open up this new avenue. Patients who are no more suitable for peritoneal dialysis may become candidates to continue peritoneal dialysis if this possibility could be realized. Additionally, patients with preference toward ambulatory peritoneal dialysis may continue to do so if pharmacological agents could be identified to modify the membrane function.

In view of the forgoing, an objective of the present disclosure is to provide a device which can be connected to a catheter through which a sensor wire can be introduced aseptically with real-time sensing and analysis capabilities. The device permits concurrent peritoneal dialysis while the sensor wire is inserted through the catheter inside the peritoneal cavity.

BRIEF SUMMARY OF THE INVENTION

According to a first aspect, the present disclosure relates to a real-time analyte sensing device that can be connected to a peritoneal catheter and/or inserted through a peritoneal catheter; the peritoneal catheter having a first flexible tube with a catheter inflow-outflow port at a first end, and a first connection opening at a second end; a second flexible tube with an attachment for an intraperitoneal catheter at a first end and a second connection opening at a second end; a 3-way port, wherein a first port of the 3-way port is connected to the first connection opening and a second port of the 3-way port is connected to the second connection opening; at least one flow regulation valve is connected to the inflow-outflow port; and an anti-reflux valve, connected to the third port of the 3-way port; and an analyte sensor connected to a sensor wire at a first end by a sensor connector, wherein the sensor wire has a second end that is a data connector, and wherein the analyte sensor protrudes through the anti-reflux valve and is connected to the 3-way port via the anti-reflux valve.

In some embodiments, the analyte sensor is extendable and retractable from the interior of the second flexible tube of the peritoneal catheter, wherein the analyte sensor moves through the anti-reflux valve and the 3-way port into the interior of the second flexible tube.

In some embodiments, the analyte sensor is a detector of fluid albumin, a detector of proteins, a urea detector, a sodium detector, a creatinine detector, a calcium detector, a glucose meter, a pH sensor, a viral particle sensor, a bacterial particle sensor, temperature sensor and a nucleic acid sensor.

In some embodiments, the analyte sensor is a nanowire sensor.

In some embodiments, the catheter further includes circuitry connected to the data connector.

In some embodiments, the circuitry is configured to analyze data received from the analyte sensor.

In some embodiments, the flow regulation valve comprises an electronic switch, a toggle switch, a solenoid valve, and a diaphragm valve and the flow regulation valve is configured to automatically switch from an inflow setting and an outflow setting, and to configure a flow rate.

In some embodiments, the catheter further includes a filter in the inflow/outflow port.

In some embodiments, the sensor wire is shielded by a coating.

In some embodiments, the coating is nonconductive.

In some embodiments, the first flexible tube and the second flexible tube have a non-stick coating on an interior of the tube.

In some embodiments, the flow regulation valve is a solenoid valve or a diaphragm isolation valve.

In some embodiments, the flow regulation valve is connected to a pump.

According to a second aspect, the present disclosure relates to a method of changing a dialysis protocol in a patient undergoing peritoneal dialysis with an intraperitoneal catheter implanted in the patient, including connecting the peritoneal catheter that is described herein, to an intraperitoneal catheter in the patient and connecting the data connector of the catheter to the circuitry, wherein the circuitry is configured to analyze data received from the analyte sensor, sensing a fluid and determining a level of analytes in the fluid from the data, which is sent as an output signal by the analyte sensor, and changing the dialysis protocol based on the data received from the analyte sensor.

In some implementations of the method, changing the dialysis protocol is modulating a pump action of a pump based on the output signal.

In some implementations of the method, the pump action may be to stop the pump, or change a pump flow.

In some implementations of the method, the peritoneal dialysis is a continuous ambulatory peritoneal dialysis or automated peritoneal dialysis.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
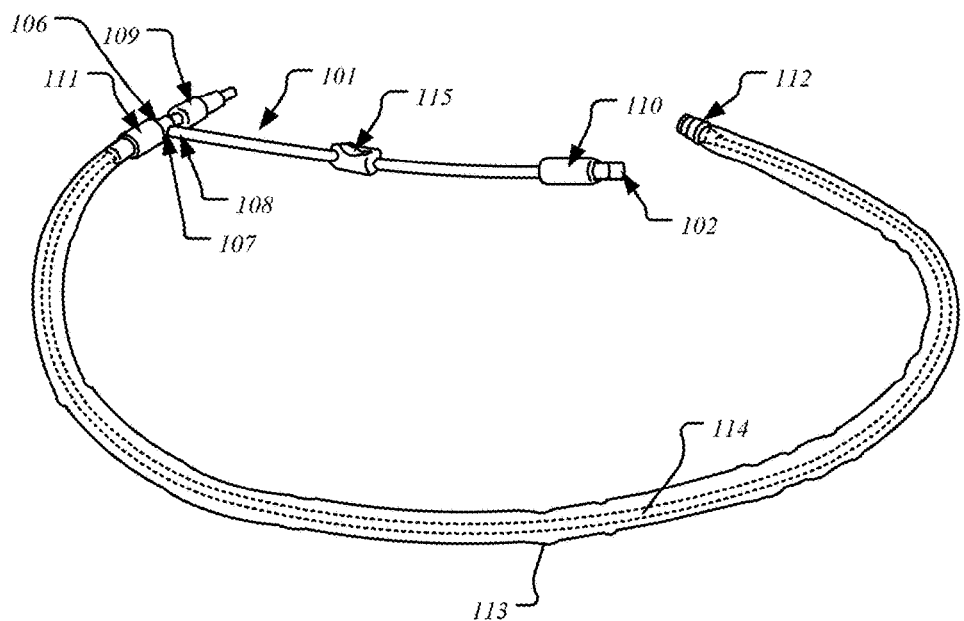
FIG. 1 is a view of a peritoneal dialysis catheter and wiring.

Referring now to the drawings, wherein like reference numerals designate identical or corresponding parts throughout the several views.

Figure 2:
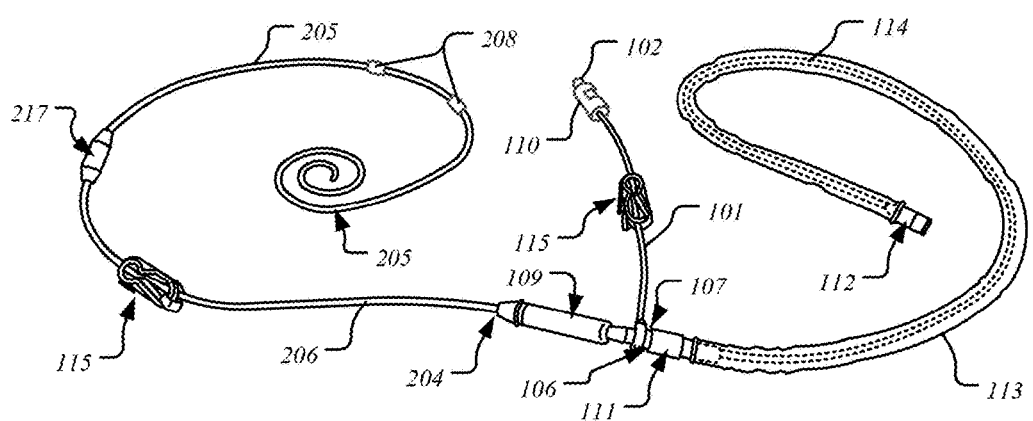
FIG. 2 is an alternate view of the peritoneal dialysis catheter device attached to a peritoneal dialysis catheter via an extension set.

An aspect of the present disclosure relates to a device which allows aseptic insertion of a sensor wire through a peritoneal dialysis catheter for real-time analyte sensing in the peritoneal fluid in vivo. Referring to FIG. 1 the device includes a first flexible tube 101 having two ends. A first end is a catheter inflow-outflow port 110, which when not in use is capped 102, and a second end is a first connection opening. Referring to FIG. 2 the device further includes a second flexible tube 206 having two ends. A first end of the second flexible tube is an attachment 217 to connect to the peritoneal dialysis catheter 205 and a second end of the second flexible tube is a second connection opening 204. The second flexible tube may be referred to as an extension set. The device further includes a 3-way port 107. A first port 108 of the 3-way port is connected to the first connection opening of the first flexible tube 101 and a second port 109 of the 3-way port is connected to the second connection opening 204 of the second flexible tube 206. An intraperitoneal catheter 205 may connect to the second flexible tube 206 at the attachment 217. At least one flow regulation valve 110 is connected to the inflow-outflow port 102. The device further includes an anti-reflux valve 111, connected to the third port 106 of the 3-way port 107. The device further includes an analyte sensor. The analyte sensor is inside the cavity of the anti-reflux valve and so is not visible in the figures. The analyte sensor is connected to a sensor wire 114 at one end by a sensor connector and the sensor wire 114 has a second end that is data connector 112. The sensor wire may have a covering 113 such as a tube or bag surrounding the wire 114. The analyte sensor is connected to the 3-way port 107 via the anti-reflux valve 111 and the analyte sensor protrudes through the anti-reflux valve 111 in a direction into the 3-way port. In some embodiments, the peritoneal catheter may include a clamp 115, which may stop or allow the flow of dialysate. Cuffs 208 are depicted in FIG. 2 are shown for demonstration purpose here. When the peritoneal dialysis catheter s in situ, these cuffs lie buried in the abdominal wall of the patient and are not visible. They help in securing peritoneal dialysis catheter and prevent migration of catheter and infection.

In some embodiments, the 3-way port 107 may connect to the first flexible tube 101, the second flexible tube 206 and the anti-reflux valve 111 by fittings including, but not limited to a tube-to-tube barbed fitting, threaded fitting, Luer lock fittings, or quick-connect fittings. The 3-way port and the fittings may comprise nylon, polypropylene, polycarbonate, PVDF, or silicone. In some embodiments, the analyte sensor may be placed into the anti-reflux valve 111 by a threaded coupling, luer lock coupling or a quick-connect coupling to secure it inside the anti-reflux valve 111. All points of attachment between the 3-way port may further include silicone washers to prevent leaking.

In some embodiments, the analyte sensor extends into the second flexible tube 206 through the 3-way port 107. In some embodiments, the analyte sensor may be permanently fixed to the inside of the second flexible tube 206. In some embodiments, the wire 114 may be disconnected from the analyte sensor when not n use by a patient.

In some embodiments, the first flexible tube 101 and the second flexible tube 206 have a non-stick coating on an interior of the tube. The non-stick coating may include, but is not limited to a polyurethane coating, such as one described in U.S. Pat. No. 6,724,223, a siloxane coating, a poly(N-vinylpyrrolidone) polymer, or coatings described in U.S. Pat. No. 5,919,570.

In some embodiments, the tubing (i.e. the first flexible tube 101 and the second flexible tube 206) may be standard sized medical tubing for peritoneal dialysis such as 2 mm to 15 mm, 3 mm to 10 mm, or 4 mm to 7 mm inner diameter flexible tubing. The tubing may comprise PVC, polyethylene, nylon, or polytetrafluoroethylene. The tubing may be 5 cm to 15 cm long but may include longer lengths for applications in which the wire is coiled or partially coiled.

Rapid development in technology and miniaturization has resulted in development of low energy analyte sensors. The technology is currently being utilized in the management of diabetes mellitus and to monitor sweat electrolytes in athletes. See Yi Cui et al. Nanowire nanosensors for highly sensitive and selective detection of biological and chemical species. Science 293, 1289 (2001); DOI: 10.1126/science.1062711; Michael C. McAlpine, Habib Ahmad, Dunwei Wang & James R. Heath. Highly ordered nanowire arrays on plastic substrates for ultTasensitive flexible chemical sensors. Nature Materials. 2007: 6; 379-384; Wei Gao, Sam Emaminejad et al. Fully integrated wearable sensor arrays for multiplexed in situ perspiration analysis. Nature. 2016: 529, 509-514, each incorporated herein in their entirety. Having real-time sensing enables the presently disclosed catheter to receive feedback from peritoneal dialysis fluid in vivo. In some embodiments, the analyte sensor is a nanowire sensor. In some embodiments, the analyte sensor is a paper microfluidic sensor. In some embodiments, the analyte sensor measures field effect based on interactions with analytes as described herein. See J. M. Nassar, M. D. Cordero, A. T. Kutbee, M. A. Karimi, G. A. Torres Sevilla, A. M. Hussain, A. Shamim, M. M. Hussain, "Paper Skin Multi-Sensory Platform for Simultaneous Environmental Monitoring", Adv. Mater. Tech. (Wiley-VCH) and N. S. Oliver, C. Toumazou, A. E. G. Cass and D. G. Johnston, "Glucose sensors: a review of current and emerging technology," Diabet Med. 2009 March; 26(3):197-210, each incorporated herein by reference in their entirety.

In order to gather readings for the real-time sensing the peritoneal catheter includes an analyte sensor in some embodiments, the analyte sensor is a detector of fluid albumin, a detector of proteins, a glucose meter, a pH sensor, a viral particle sensor, a bacterial particle sensor, and a nucleic acid sensor. The analyte sensor may further detect p-cresol, urea, sodium, potassium, glucose, homocysteine, nitrate, AGE (advanced glycation end products), or hippouric acid. The analyte sensor may have a limit of detection of 1 part per billion to 900 part per million, 100 parts per billion to 500 parts per million, 500 part per billion to 100 parts per million, or 900 parts per billion to 1 part per million or within the range as observed in health and disease in patients with renal failure. The glucose sensor may have a limit of detection from 3 mmol/L to 500 mmol/L.

The sensor wire 114 will have the analyte sensor on the tip to be inserted through the anti-reflux valve 111 of the peritoneal catheter. In some embodiments, the catheter further includes circuitry connected to the data connector 112. The circuitry may further be connected to a battery pack, data storage and a data communication device, which may be integrated into one unit. In some embodiments, the circuitry is configured to analyze data received from the analyte sensor.

In some embodiments, the sensor wire may have a non-stick coating, as described herein for the interior of the first flexible tube and second flexible tube, for ease of placement through the peritoneal dialysis catheter. In some embodiments the sensor wire 114 is shielded by the coating. In some embodiments, the wire will be sterile and contained in a sterilized and sealed plastic bag 113 and/or tube when retracted from the intraperitoneal catheter and the first flexible tube. The bag and/or tube 113 may comprise vinyl, polyethylene, or polytetrafluoroethyene. The bag and/or tube may be shaped as a hollow cylinder that is secured to the anti-reflux valve by clamps or a threaded coupling and may be the 2 times to 3 times the length of the wire. The bag and/or tube is not bonded to the wire. In some embodiments the bag or tube may be loosely surround the wire and may be secured around the wire by securing to the third port 106 of the 3-way port 107 by a threaded fitting or other fitting compatible with the third port 106. The bag and/or tube 113 thereby contracts as the wire 114 extends into the second flexible tube 206, and expands as the wire 114 is retracted from the second flexible tube. The bag and/or tube will be kept sterile by the coating further being anti-microbial. In some embodiments, the coating is nonconductive. The nonconductive coating may include, but is not limited to nylon, Teflon PTFE, and polyester.

In some embodiments, the analyte sensor is extendable and retractable from the interior of the second flexible tube of the peritoneal catheter by going through the anti-reflux valve and the 3-way port. The analyte sensor may be on a telescopic mechanism, coiling mechanism, or winding mechanism that is attached to a motor that may extend the analyte sensor to contact dialysis fluid within the peritoneal cavity of a patient. The motor may be connected and controlled by signals from circuitry employed as described herein. The analyte sensor, when fully deployed, may extend 1 cm to 20 cm, 5 cm to 15 cm, or 8 cm to 10 cm. n some implementations, the analyte sensor may extend 1 cm to 5 cm, or 2 cm to 3 cm beyond the tell final hole of peritoneal dialysis catheter.

The circuitry of the peritoneal catheter may be configured to controla variety of changes to a peritoneal dialysis protocol while a patient is undergoing dialysis. For example, for patients who may have existing peritoneal dialysis catheter implanted, the presently disclosed catheter may guide renal physicians to determine appropriate dwell time. Dwell time is a duration peritoneal dialysis fluid should stay inside the peritoneal cavity before the cavity is flushed. The circuitry may be further configured to determine a number of exchanges of fluids to maximize the benefit from this form of renal replacement therapy. The exchange may be the number of times the peritoneal dialysis fluid may be injected into the peritoneum and flushed from the peritoneum. The benefit of the presently disclosed catheter is that exchanges may be performed while the device is in place on the patient, reducing disturbance to the patient. Further the circuitry may be configured to transmit a signal to alert a physician or caregiver to change a prescription in real time, based on data received from the analyte sensors and processed by the circuitry. The circuitry may determine that the prescription of ingredients of the dialysis fluid or dialysate may need to change. Ingredients which may change include, but are not limited to glucose (dextrose), sucrose, potassium, chloride, sodium, calcium, magnesium, lactate, icodextrin and bicarbonate.

In some embodiments, the circuitry may be configured to modulate the flow regulation valve to automatically switch from an inflow setting and an outflow setting, and to configure a flow rate. The flow regulation valve may be modulated by an electronic switch that may be adjusted by the circuitry. In some embodiments, the flow regulation valve may have a toggle switch that may be manually adjusted. In some embodiments, the flow regulation valve is a solenoid valve or a diaphragm isolation valve. In some embodiments, the flow regulation valve is connected to a pump. The pump may be a pneumatic pump, a diaphragm pump, or a syringe driven pump.

In some embodiments, the catheter further includes a filter in the inflow-outflow port. The filter may be a polypropylene filter, a hydrophobic filter, a PVC filter or a combination thereof. The filter may have a porosity of less than 100 micron, less than 50 micron, less than 25 micron, less than 15 micron, less than 10 micron, less than 8 micron, or less than 5 micron. The filter may be an inline filter in series or in parallel.

According to a second aspect, a method of changing a dialysis protocol in a patient undergoing peritoneal dialysis and having a intraperitoneal catheter implanted, including connecting the peritoneal catheter that is described herein, to an intraperitoneal catheter in the patient and connecting the data connector of the peritoneal catheter to the circuitry, wherein the circuitry s configured to analyze data received from the analyte sensor and sensing fluid and determining a level of analytes from the data, which is sent as an output signal; and changing the dialysis protocol based on the data received from the analyte sensor. The circuitry may be further connected with automated valves of containers of various ingredients employed in the dialysate as described herein. Based on the analyte sensor data, the dialysis protocol may be changed by changing the flow rate, changing a concentration of the ingredients of a dialysate as described herein. The sensing of the fluid include extending the analyte sensor through anti-reflux valve and the 3-way port and into the second flexible tube. In some implementations, the analyte sensor may extend into the intraperitoneal catheter and into the peritoneal cavity.

In some implementations of the method, the changing of the dialysis protocol is modulating a pump action of the pump based on the output signal. Modulating a pump action may include an output signal that is received by a pump having pump circuitry configured to translate the output signal from the circuitry connected to the analyte sensor and modulate a pump action. In some implementations of the method, the pump action may be to stop the pump, or change a pump flow. The pump may be connected to a volume of dialysate that is clean and a used volume of dialysate to pump to and from the peritoneal cavity of a patient.

The determining may be described as a series of comparisons of data and a baseline data stored in a memory of the circuitry. For example the determining may be a comparison of glucose levels. If a glucose level exceeds a predetermined threshold value of glucose, the signal may include information to change the glucose content of the next phase of the dialysate injected for the dialysis protocol. For example a high glucose threshold level may be 300 mmol/L to 500 mmol/L and a low glucose threshold level may be 2.5 mmol/L to 4.0 mmol/L each of which may signal the circuitry to modify the glucose content of the next phase of dialysate. The circuitry may send a signal that controls the volume of glucose liquid that is injected into the dialysis fluid before the fluid is injected through the first flexible tube into the second flexible tube and into the peritoneum. A threshold of a low pH in the fluid may be 6.5 and a threshold of high pH may be 7.4. Exemplary low threshold values for protein in the dialysate may be 0.5 g/dL to 1.1 g/dL and an exemplary high threshold for protein in the dialysate may be 4.5 g/dL to 10 g/dL. Other analytes mentioned may have high and low threshold values which vary by patient and may be adjusted by a physician familiar in the art.

The circuitry employed by the presently disclosed peritoneal dialysis catheter may include data communication by wireless or wired connections including internet protocols, Bluetooth or other data communication protocols familiar in the art. Further the circuitry may prevent a dialysis protocol from continuing if an emergency arises. For example the analyte sensor may detect a sudden flux in pH or glucose, causing a signal to be sent to the circuitry connected with the catheter through the data connecter and then the circuitry can signal the pumps to empty the peritoneum by adjusting the inflow-outflow valve to outflow the dialysate. In some embodiments the circuitry may further send a signal to notify the physician or the caregiver of an emergency. In some implementations, the circuitry may generate an audible or visual signal and continue a current protocol until a physician or caregiver generates a signal by wireless or wired communications, such as acknowledging the audible or visual signal on an application on a phone or smart device, or to enter specific instructions into an input/output device (i.e. keyboard, touchscreen, mouse click, remote, etc) to communicate with the circuitry to change the volume of the dialysate, a flow rate of the dialysate, a dwell time (i.e. a length of time to keep the dialysis fluid in a patient's peritoneum before draining), or a prescription of the dialysate.

An exemplary method includes employing the described device for patients who have a peritoneal dialysis catheter in place in their abdomen. The data connector cap may be removed on the sensor wire to connect with the circuitry. The analyte sensor attached to the sensor wire (which is covered by plastic sleeve) is threaded through the anti-reflux valve, the 3-way port, the second flexible tube, and through the peritoneal dialysis catheter until it reaches the peritoneal cavity. In some instances, a peritoneal dialysis fluid bag may be connected to the first flexible tube and flushed. A prescribed volume (a dwell volume) is retained in the peritoneal cavity. The sensor begins sensing the fluid and transmits the data to the circuitry. The sensor measures a level of each of the analytes (urea, glucose, sodium, potassium, protein, lactate, icodextrin, pH and nitrate). The data may be stored and processed in the circuitry and may be transferred to the physician or caregiver via WiFi, Bluetooth®, or by a data storage device such as a USB flash drive, SIM card, SD card, or the like. The data could also be stored or transmitted through mobile application in a tablet or smartphone device connected by Bluetooth® technology to the circuitry. This data may be analyzed to understand peritoneal membrane characteristics such as ultrafiltration rate and apex time or other characteristics familiar to those knowledgeable in the art.

Figure 3:
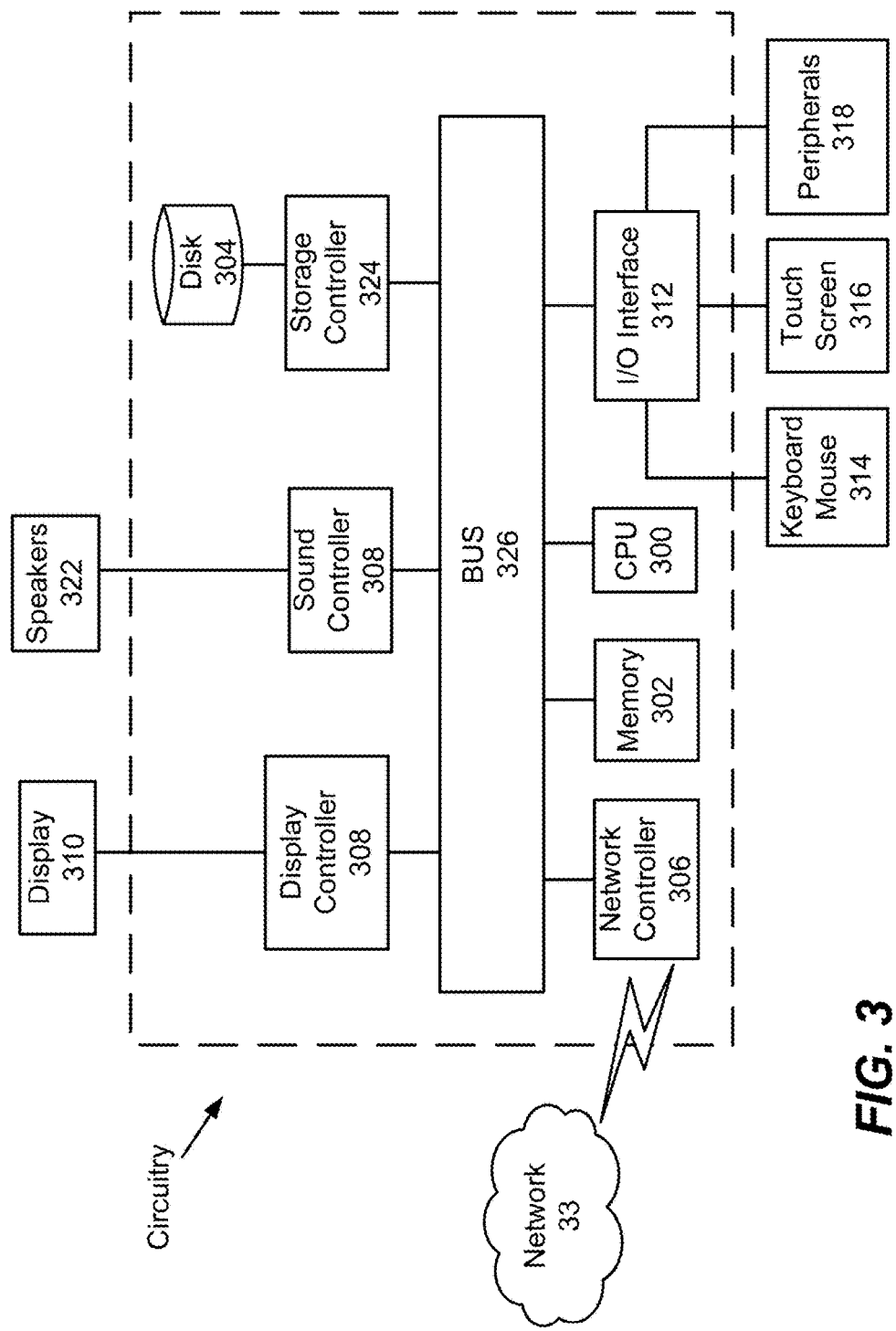
FIG. 3 is a hardware description of the circuitry according to exemplary embodiments.

Next, a hardware description of the circuitry according to exemplary embodiments is described with reference to FIG. 3. In FIG. 3, the circuitry includes a CPU 300 which performs the processes described above/below. The process data and instructions may be stored in memory 302. These processes and instructions may also be stored on a storage medium disk 304 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM EEPROM, hard disk or any other information processing device with which the circuitry communicates, such as a server or computer.

Further, the claimed advancements may be provided as a utility application, background daemon, or component of an operating system, or combination thereof, executing in conjunction with CPU 300 and an operating system such as Microsoft Windows 7, UNIX, Solaris, LINUX, Apple MAC-OS and other systems known to those skilled in the art.

The hardware elements in order to achieve the circuitry may be realized by various circuitry elements, known to those skilled in the art. For example, CPU 300 may be a Xenon or Core processor from Intel of America or an Opteron processor from AMD of America, or may be other processor types that would be recognized by one of ordinary skill in the art. Alternatively, the CPU 300 may be implemented on an FPGA, ASIC, PLD or using discrete logic circuits, as one of ordinary skill in the art would recognize. Further, CPU 300 may be implemented as multiple processors cooperatively working in parallel to perform the instructions of the inventive processes described above.

The circuitry in FIG. 3 also includes a network controller 306, such as an Intel Ethernet PRO network interface card from Intel Corporation of America, for interfacing with network 33. As can be appreciated, the network 33 can be a public network, such as the Internet, or a private network such as an LAN or WAN network, or any combination thereof and can also include PSTN or ISDN sub-networks. The network 33 can also be wired, such as an Ethernet network, or can be wireless such as a cellular network including EDGE, 3G and 4G wireless cellular systems. The wireless network can also be WiFi, Bluetooth, or any other wireless form of communication that is known.

The circuitry further includes a display controller 308, such as a NVIDIA GeForce GTX or Quadro graphics adaptor from NVIDIA Corporation of America for interfacing with display 310, such as a Hewlett Packard HPL2445w LCD monitor. A general purpose I/O interface 312 interfaces with a keyboard and/or mouse 314 as well as a touch screen panel 316 on or separate from display 310. General purpose I/O interface also connects to a variety of peripherals 318 including printers and scanners, such as an OfficeJet or DeskJet from Hewlett Packard.

A sound controller 320 is also provided in the circuitry, such as Sound Blaster X-Fi Titanium from Creative, to interface with speakers/microphone 322 thereby providing sounds and/or music.

The general purpose storage controller 324 connects the storage medium disk 304 with communication bus 326, which may be an ISA, EISA, VESA, PCI, or similar, for interconnecting all of the components of the circuitry. A description of the general features and functionality of the display 310, keyboard and/or mouse 314, as well as the display controller 308, storage controller 324, network controller 306, sound controller 320, and general purpose I/O interface 312 is omitted herein for brevity as these features are known.

The exemplary circuit elements described in the context of the present disclosure may be replaced with other elements and structured differently than the examples provided herein.

In some implementations, the circuitry may modify the peritoneal dialysis fluid volume or dwell time inside the patient's body based on data received from the analyte sensor.

In some implementations, several cycles of fluid exchanges may be performed for a patient with different prescriptions. Data received by the analyte sensor may assist a physician in determining an optimum prescription. In some implementations of the method, a different dialysis fluid may be selected to flow through the pump based on the output signal.

Patients who may benefit from the presently described peritoneal catheter may have renal diseases or renal dysfunction. In some implementations, the patient may be undergoing continuous ambulatory peritoneal dialysis or automated peritoneal dialysis.

The invention claimed is:

1. A real-time analyte sensing device comprising:
an intraperitoneal catheter,
a first flexible tube,
a second flexible tube,
a T-shaped 3-way port having a first, second and third port,
a first and a second clamp,
a flow regulation valve,
an antireflux valve,
a sensor wire and covering, and
data connector;
wherein:
the intraperitoneal catheter is attached to a distal end of the second flexible tube which comprises the first clamp,
the proximal end of the second flexible tube is connected to the second port of the 3-way port,
the first flexible tube comprises the second clamp and is radially attached to the first port of the 3-way port,
the distal end of the first flexible tube is attached via the flow regulation valve to the catheter inflow-outflow port,
the antireflux valve is axially attached to the third port of the 3-way port, and
the data connector is attached to a distal end of the sensor wire and covering, the sensor wire and covering is axially attached to a distal end of the antireflux valve.

2. The device of claim 1, wherein the sensor wire is extendable into the interior of the second flexible tube through the anti-reflux valve and the 3-way port and wherein the sensor wire may be retracted from the interior of the second flexible tube through the 3-way port and antireflux valve.

3. The device of claim 1, wherein the analyte sensor detects at least one of temperature, pH, calcium, sodium, glucose, creatinine, fluid albumin, protein, or nucleic acid.

4. The device of claim 3, wherein the analyte sensor is a nanowire sensor.

5. The device of claim 1, further comprising circuitry connected to the data connector.

6. The device of claim 5, wherein the circuitry is configured to analyze data received from the analyte sensor.

7. The device of claim 1, wherein the flow regulation valve comprises at least one of an electronic switch, a toggle switch, a solenoid valve, or a diaphragm valve, and wherein the flow regulation valve is configured to automatically switch from an inflow setting and an outflow setting, and to configure a flow rate.

8. The device of claim 1, wherein the inflow/outflow port further comprises a filter.

9. The device of claim 1, wherein the sensor wire is shielded by a coating.

10. The device of claim 9, wherein the coating is nonconductive.

11. The device of claim 1, wherein the first flexible tube and the second flexible tube have a non-stick coating on an interior of the tube.

12. The device of claim 1, wherein the flow regulation valve is a solenoid valve or a diaphragm isolation valve.

13. The device of claim 1, wherein the flow regulation valve is connected to a pump.

14. A method for adjusting a dialysis protocol in a patient undergoing peritoneal dialysis with an intraperitoneal catheter, comprising:
implanting the device of claim 1 into a patient,
detecting at least one analyte in the patient, and
adjusting the dialysis protocol based on a level of analytes detected.

15. The method of claim 14, wherein changing the dialysis protocol is modulating a pump action of a pump based on the output signal.

16. The method of claim 15, wherein the pump action may be to stop the pump, or change a pump flow.

17. The method of claim 14, wherein the peritoneal dialysis is a continuous ambulatory peritoneal dialysis or automated peritoneal dialysis.

\* \* \* \* \*